United States Patent
Abrahamov

(10) Patent No.: US 10,300,119 B2
(45) Date of Patent: May 28, 2019

(54) COMPOSITIONS AND METHODS FOR PREVENTING INJURY DURING OR RESULTING FROM CARDIAC SURGERY

(71) Applicant: Mor Research Applications Ltd., Tel Aviv (IL)

(72) Inventor: Dan Abrahamov, Tel Aviv (IL)

(73) Assignee: MOR Research Applications Ltd., Tel Aviv (IL)

( * ) Notice: Subject to any disclaimer, the term of this patent is extended or adjusted under 35 U.S.C. 154(b) by 298 days.

(21) Appl. No.: 14/891,415

(22) PCT Filed: May 12, 2014

(86) PCT No.: PCT/IL2014/050421
§ 371 (c)(1),
(2) Date: Nov. 16, 2015

(87) PCT Pub. No.: WO2014/184794
PCT Pub. Date: Nov. 20, 2014

(65) Prior Publication Data
US 2016/0089423 A1    Mar. 31, 2016

Related U.S. Application Data

(60) Provisional application No. 61/823,655, filed on May 15, 2013.

(51) Int. Cl.
*A61K 38/57*    (2006.01)
*A61K 9/00*    (2006.01)
*A61K 45/06*    (2006.01)

(52) U.S. Cl.
CPC ........... *A61K 38/57* (2013.01); *A61K 9/0019* (2013.01); *A61K 45/06* (2013.01)

(58) Field of Classification Search
None
See application file for complete search history.

(56) References Cited

U.S. PATENT DOCUMENTS

| 6,924,267 | B2 * | 8/2005 | Daemen | A61K 38/1709 435/1.1 |
| 7,704,958 | B1 | 4/2010 | Shapiro | |
| 2004/0220239 | A1 * | 11/2004 | Shapiro | A61K 31/00 514/362 |
| 2005/0075597 | A1 * | 4/2005 | Vournakis | A61L 15/44 604/4.01 |
| 2005/0277106 | A1 | 12/2005 | Daemen et al. | |
| 2011/0319330 | A1 | 12/2011 | Shapiro | |

FOREIGN PATENT DOCUMENTS

| WO | 2005112989 A1 | 12/2005 |
| WO | 2012178102 A2 | 12/2012 |
| WO | 2013106589 A1 | 7/2013 |

OTHER PUBLICATIONS

Gao W. Thesis from U of Toronto: The Effect of Alpha 1 Antitrypsin on Ischemia Reperfusion Injury in Lung Transplantation Nov. 2012, 89 pages. (Year: 2012).*
Toldo S. et al. Alpha 1 Antitrypsin Inhibits Caspase-1 and Protects from Acute Myocardial Ischemia Reperfusion Injury. J of Molecular and Cellular Cardiology 51(2)244-251, May 2011. (Year: 2011).*
Lambert C. et al. The Treatment of Postperfusion Bleeding Using Aminocaproic Acid . . . Annals of Thoracic Surgery 28(5)440-444, Nov. 1979. (Year: 1979).*
Gao Wenxi 'The Effect of Alpha 1-Antitrypsin on Ischemia-Reperfusion Injury in Lung Transplantation' Diss. University of Toronto, [Online] Nov. 20, 2012 (89 pages).
Toldo, Stefano et al.: 'Alpha-1 antitrypsin inhibits caspase-1 and protects from acute myocardial ischemia-reperfusion injury.' Journal of Molecular and Cellular Cardiology vol. 51, No. 2, May 12, 2011, pp. 244-251 (9 pages).
http://alpha-1foundation.org/augmentation-therapy (for purposes of this IDS, the publication date is presumed to be Nov. 15, 2015 or earlier) (5 pages).
http://www.kamada.com/alpha1.php?ID=4 (for purposes of this IDS, the publication date is presumed to be Nov. 15, 2015 or earlier) (2 pages).
Pickering NJ, et al., "The behavior of antithrombin III, alpha 2 macroglobulin, and alpha 1 antitrypsin during cardiopulmonary bypass." Am J Clin Pathol, 1983; 80(4): 459-64. [Abstract only] (1 page).
Grano, G., et al., "reduction of active elastase concentration by means of immobilized inhibitors: a novel therapeutic approach." Biotech Progress, 2004; 20(3): 968-974. [Abstract only] (2 pages).
Kamimoto Y. et al.; 'Plasma clearance of intravenously injected aspartate aminotransferase isozymes: Evidence for preferential uptake by sinusoidal liver cells'. Hepatology. May-Jun. 1985; vol. 5 (3), pp. 367-375. (9 pages).

\* cited by examiner

*Primary Examiner* — Ralph J Gitomer
(74) *Attorney, Agent, or Firm* — Roach Brown McCarthy & Gruber, P.C.; Kevin D. McCarthy

(57) ABSTRACT

Disclosed herein are compositions and methods for treating damage inflicted by use of a cardio-pulmonary bypass (CPB) machine, particularly excessive bleeding and multi organ failure, by administering a pharmaceutical composition comprising alpha-1 antitrypsin (AAT).

15 Claims, No Drawings
Specification includes a Sequence Listing.

SEQUENCE LISTING

```
<160> NUMBER OF SEQ ID NOS: 2

<210> SEQ ID NO 1
<211> LENGTH: 3220
<212> TYPE: DNA
<213> ORGANISM: Homo sapiens

<400> SEQUENCE: 1
acaatgactc ctttcggtaa gtgcagtgga agctgtacac tgcccaggca aagcgtccgg      60
gcagcgtagg cgggcgactc agatcccagc cagtggactt agcccctgtt tgctcctccg     120
ataactgggg tgaccttggt taatattcac cagcagcctc ccccgttgcc cctctggatc     180
cactgcttaa atacggacga ggacagggcc ctgtctcctc agcttcaggc accaccactg     240
acctgggaca gtgaatcgac aatgccgtct tctgtctcgt ggggcatcct cctgctggca     300
ggcctgtgct gcctggtccc tgtctccctg gctgaggatc cccagggaga tgctgcccag     360
aagacagata catcccacca tgatcaggat cacccaacct tcaacaagat caccccccaac    420 ctggctgagt tcgccttcag cctataccgc cagctggcac accagtccaa cagcaccaat    480
atcttcttct ccccagtgag catcgctaca gcctttgcaa tgctctccct ggggaccaag    540
gctgacactc acgatgaaat cctggagggc ctgaatttca acctcacgga gattccggag    600
gctcagatcc atgaaggctt ccaggaactc ctccgtaccc tcaaccagcc agacagccag    660
ctccagctga ccaccggcaa tggcctgttc ctcagcgagg gctgaagct agtggataag    720 tttttggagg atgttaaaaa gttgtaccac tcagaagcct tcactgtcaa cttcggggac    780
accgaagagg ccaagaaaca gatcaacgat tacgtggaga agggtactca agggaaaatt    840
gtggatttgg tcaaggagct tgacagagac acagttttg ctctggtgaa ttacatcttc    900
tttaaaggca aatgggagag acccttgaa gtcaaggaca ccgaggaaga ggacttccac    960
gtggaccagg tgaccaccgt gaaggtgcct atgatgaagc gtttaggcat gtttaacatc   1020
cagcactgta agaagctgtc cagctgggtg ctgctgatga aatacctggg caatgccacc   1080
gccatcttct tcctgcctga tgaggggaaa ctacagcacc tggaaaatga actcacccac   1140
gatatcatca ccaagttcct ggaaaatgaa gacagaaggt ctgccagctt acatttaccc   1200
aaactgtcca ttactggaac ctatgatctg aagagcgtcc tgggtcaact gggcatcact   1260
aaggtcttca gcaatgggc tgacctctcc ggggtcacag aggaggcacc cctgaagctc   1320
tccaaggccg tgcataaggc tgtgctgacc atcgacgaga aagggactga agctgctggg   1380
gccatgtttt tagaggccat accatgtct atccccccg aggtcaagtt caacaaaccc   1440
```

```
tttgtcttct taatgattga acaaaatacc aagtctcccc tcttcatggg aaaagtggtg    1500
aatcccaccc aaaaataact gcctctcgct cctcaacccc tccccctccat ccctggcccc   1560 ctccctggat gacattaaag aagggttgag ctggtccctg cctgcatgtg actgtaaatc   1620
cctcccatgt tttctctgag tctcccttt g cctgctgagg ctgtatgtgg gctccaggta   1680
acagtgctgt cttcgggccc cctgaactgt gttcatggag catctggctg ggtaggcaca   1740
tgctgggctt gaatccaggg gggactgaat cctcagctta cggacctggg cccatctgtt   1800
tctggagggc tccagtcttc cttgtcctgt cttggagtcc caagaagga atcacagggg    1860 aggaaccaga taccagccat gaccccaggc tccaccaagc atcttcatgt cccctgctc    1920 atcccccact ccccccccacc cagagttgct catcctgcca gggctggctg tgcccacccc   1980
aaggctgccc tcctggggc cccagaactg cctgatcgtg ccgtggccca gttttgtggc    2040
atctgcagca acacaagaga aggacaatg tcctcctctt gacccgctgt cacctaacca    2100
gactcgggcc ctgcacctct caggcacttc tggaaaatga ctgaggcaga ttcttcctga    2160
agcccattct ccatggggca acaaggacac ctattctgtc cttgtccttc catcgctgcc    2220
ccagaaagcc tcacatatct ccgtttagaa tcaggtccct tctccccaga tgaagaggag   2280
ggtctctgct ttgttttctc tatctcctcc tcagacttga ccaggccag caggccccag    2340 aagaccatta ccctatatcc cttctcctcc ctagtcacat ggccataggc ctgctgatgg    2400
ctcaggaagg ccattgcaag gactcctcag ctatgggaga ggaagcacat cacccattga   2460 ccccccgcaac ccctccct tt cctcctctga gtcccgactg gggccacatg cagcctgact   2520
tctttgtgcc tgttgctgtc cctgcagtct tcagagggcc accgcagctc cagtgccacg   2580
gcaggaggct gttcctgaat agcccctgtg gtaagggcca ggagagtcct tccatcctcc    2640
aaggccctgc taaaggacac agcagccagg aagtcccctg gcccctagc tgaaggacag    2700 cctgctccct ccgtctctac caggaatggc cttgtcctat ggaaggcact gccccatccc    2760
aaactaatct aggaatcact gtctaaccac tcactgtcat gaatgtgtac ttaaaggatg    2820
aggttgagtc ataccaaata gtgatttcga tagttcaaaa tggtgaaatt agcaattcta    2880
catgattcag tctaatcaat ggataccgac tgtttcccac acaagtctcc tgttctctta    2940
agcttactca ctgacagcct ttcactctcc acaaatacat taaagatatg gccatcacca   3000 agcccctag gatgacacca gacctgagag tctgaagacc tggatccaag ttctgacttt    3060 tcccctgac agctgtgtga ccttcgtgaa gtcgccaaac ctctctgagc cccagtcatt   3120
gctagtaaga cctgcctttg agttggtatg atgttcaagt tagataacaa aatgtttata   3180
cccattagaa cagagaataa atagaactac atttcttgca                          3220
```

<210> SEQ ID NO 2
<211> LENGTH: 418
<212> TYPE: PRT
<213> ORGANISM: Homo sapiens

<400> SEQUENCE: 2

Met Pro Ser Ser Val Ser Trp Gly Ile Leu Leu Leu Ala Gly Leu Cys
1               5                   10                  15

Cys Leu Val Pro Val Ser Leu Ala Glu Asp Pro Gln Gly Asp Ala Ala
            20                  25                  30

Gln Lys Thr Asp Thr Ser His His Asp Gln Asp His Pro Thr Phe Asn
        35                  40                  45

Lys Ile Thr Pro Asn Leu Ala Glu Phe Ala Phe Ser Leu Tyr Arg Gln
    50                  55                  60

```
Leu Ala His Gln Ser Asn Ser Thr Asn Ile Phe Phe Ser Pro Val Ser
65                  70                  75                  80

Ile Ala Thr Ala Phe Ala Met Leu Ser Leu Gly Thr Lys Ala Asp Thr
                85                  90                  95

His Asp Glu Ile Leu Glu Gly Leu Asn Phe Asn Leu Thr Glu Ile Pro
            100                 105                 110

Glu Ala Gln Ile His Glu Gly Phe Gln Glu Leu Leu Arg Thr Leu Asn
            115                 120                 125

Gln Pro Asp Ser Gln Leu Gln Leu Thr Thr Gly Asn Gly Leu Phe Leu
        130                 135                 140

Ser Glu Gly Leu Lys Leu Val Asp Lys Phe Leu Glu Asp Val Lys Lys
145                 150                 155                 160

Leu Tyr His Ser Glu Ala Phe Thr Val Asn Phe Gly Asp Thr Glu Glu
                165                 170                 175

Ala Lys Lys Gln Ile Asn Asp Tyr Val Glu Lys Gly Thr Gln Gly Lys
            180                 185                 190

Ile Val Asp Leu Val Lys Glu Leu Asp Arg Asp Thr Val Phe Ala Leu
        195                 200                 205

Val Asn Tyr Ile Phe Phe Lys Gly Lys Trp Glu Arg Pro Phe Glu Val
    210                 215                 220

Lys Asp Thr Glu Glu Glu Asp Phe His Val Asp Gln Val Thr Thr Val
225                 230                 235                 240

Lys Val Pro Met Met Lys Arg Leu Gly Met Phe Asn Ile Gln His Cys
                245                 250                 255

Lys Lys Leu Ser Ser Trp Val Leu Leu Met Lys Tyr Leu Gly Asn Ala
            260                 265                 270

Thr Ala Ile Phe Phe Leu Pro Asp Glu Gly Lys Leu Gln His Leu Glu
            275                 280                 285

Asn Glu Leu Thr His Asp Ile Ile Thr Lys Phe Leu Glu Asn Glu Asp
    290                 295                 300

Arg Arg Ser Ala Ser Leu His Leu Pro Lys Leu Ser Ile Thr Gly Thr
305                 310                 315                 320

Tyr Asp Leu Lys Ser Val Leu Gly Gln Leu Gly Ile Thr Lys Val Phe
                325                 330                 335

Ser Asn Gly Ala Asp Leu Ser Gly Val Thr Glu Glu Ala Pro Leu Lys
            340                 345                 350

Leu Ser Lys Ala Val His Lys Ala Val Leu Thr Ile Asp Glu Lys Gly
        355                 360                 365

Thr Glu Ala Ala Gly Ala Met Phe Leu Glu Ala Ile Pro Met Ser Ile
    370                 375                 380

Pro Pro Glu Val Lys Phe Asn Lys Pro Phe Val Phe Leu Met Ile Glu
385                 390                 395                 400

Gln Asn Thr Lys Ser Pro Leu Phe Met Gly Lys Val Val Asn Pro Thr
                405                 410                 415

Gln Lys
```

COMPOSITIONS AND METHODS FOR PREVENTING INJURY DURING OR RESULTING FROM CARDIAC SURGERY

CROSS REFERENCE TO RELATED APPLICATIONS

This patent application is a U.S. National Phase filing of commonly owned PCT Application No. PCT/IL2014/050421, filed May 12, 2014, which is based on and claims the benefit of the filing date of U.S. Provisional Patent Application No. 61/823,655, filed May 15, 2013, both which are incorporated herein by reference in their entirety.

FIELD

Disclosed herein are compositions and methods for treating damage inflicted by use of a cardio-pulmonary bypass (CPB) machine, particularly excessive bleeding and multi organ failure, by administering a pharmaceutical composition comprising alpha-1 antitrypsin (AAT).

BACKGROUND

Open heart surgery using cardiopulmonary bypass (CPB) is one of the most common surgical procedures performed today. Approximately 1,000,000 operations are conducted worldwide each year, of which 500,000 are conducted in the United States alone. Use of CPB can profoundly alter haemostasis as well as injure vital organs, predisposing patients to major haemorrhagic complications and multi organ failure.

Excessive post-operative bleeding necessitating additional surgery occurs in 7% of patients undergoing CPB. Re-operation for bleeding increases hospital mortality, substantially increases post-operative hospital stay and has a sizeable effect on health care costs.

Concerns about transfusion safety, blood product shortages and increasing blood bank costs have generated increased interest in adopting risk-limiting strategies for post-operative bleeding. In order to prevent damage from CBP, several anti-inflammatory agents have been employed during cardiac surgery; and most commonly Aprotinin.

Despite its ability to reduce postoperative bleeding, the use of Aprotinin was abandoned worldwide in 2007 after studies suggesting that its use increased the risk of complications or death. Aprotinin was withdrawn from distribution because studies demonstrated a higher incidence of myocardial infarction in comparison to those treated using other available agents (such as hexacapron). Since the withdrawal of Aprotinin from use, high risk cardiac procedures are prone to high rate of post-operative bleeding. There is thus a continuing need to develop treatments which can be used in conjunction with CPB and effectively reduce post-operative blood loss.

SUMMARY

Provided herein are compositions comprising a therapeutically effective amount of alpha-1 antitrypsin (AAT-1), or a functional variant thereof, for use in preventing or treating injury to a subject during or resultant from cardiac surgery, and particularly cardiac surgery using cardiopulmonary bypass.

Additionally described herein are methods for treating or preventing injury during or resultant from cardiac surgery in a subject, such as cardiac surgery using cardiopulmonary bypass by administering to the subject a composition comprising a therapeutically effective amount of alpha-1 antitrypsin (AAT-1), or a functional variant thereof.

The foregoing and other objects, features, and advantages will become more apparent from the following detailed description.

BRIEF DESCRIPTION OF THE DESCRIBED SEQUENCES

The nucleic and/or amino acid sequences provided herewith are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file named MORR 4 2 Seq list_ST25.txt, created May 12, 2014, about 8 KB, which is incorporated by reference herein. In the accompanying sequence listing:

SEQ ID NO. 1 is the cDNA sequence of human alpha-1 antitrypsin transcript.

SEQ ID NO. 2 is the amino acid sequence of human alpha-1 antitrypsin protein.

DETAILED DESCRIPTION

I.

| Abbreviations | |
|---|---|
| AAT-1 | Alpha-1 Anti Trypsin |
| ACT | Activated Clotting Time |
| AKI | Acute Kidney Injury |
| BAL | Broncho alveolar lavage |
| CABG | Coronary Artery Bypass Grafting |
| CPB | Cardio Pulmonary Bypass |
| CVP | Central Venous Pressure |
| HBV | Hepatitis B Virus |
| HCV | Hepatitis C Virus |
| KIM | Kidney injury molecule |
| MI | Myocardial Infarction |
| N-GAL | Neutrophil gelatinase |

II. Terms

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

In case of conflict, the present specification, including explanations of terms, will control. In addition, all the materials, methods, and examples are illustrative and not intended to be limiting.

Abnormal: Deviation from normal characteristics. Normal characteristics can be found in a control, a standard for a population, etc. For instance, where the abnormal condition is an injury or physical response, such as injury resultant from cardiac surgery employing cardiopulmonary bypass, a few appropriate sources of normal characteristics might include an individual or a population standard of a collection of individuals who are not suffering from the injury or experiencing the particular physical response. Controls or standards appropriate for comparison to a sample, for the determination of abnormality, include samples believed to be normal as well as laboratory determined values, even though such values are possibly arbitrarily set, and keeping in mind that such values may vary from laboratory to laboratory. Laboratory standards and values may be set based on a known or determined population value and may be supplied in the format of a graph or table that permits easy comparison of measured, experimentally determined values.

Administration: The introduction of a composition into a subject by a chosen route. Administration of an active compound or composition can be by any route known to one of skill in the art. Administration can be local or systemic. Local administration includes routes of administration typically used for systemic administration, for example by directing intravascular administration to the arterial supply for a particular organ. Thus, in particular embodiments, local administration includes intra-arterial administration and intravenous administration when such administration is targeted to the vasculature supplying a particular organ. Local administration also includes the incorporation of active compounds and agents into implantable devices or constructs, such as vascular stents or other reservoirs, which release the active agents and compounds over extended time intervals for sustained treatment effects.

Systemic administration includes any route of administration designed to distribute an active compound or composition widely throughout the body via the circulatory system. Thus, systemic administration includes, but is not limited to intra-arterial and intravenous administration. Systemic administration also includes, but is not limited to, topical administration, subcutaneous administration, intramuscular administration, or administration by inhalation, when such administration is directed at absorption and distribution throughout the body by the circulatory system.

Cardiac surgery: Any surgical procedure involving treatment of the cardiovascular system of a subject, and which can impair or temporarily stop normal cardiovascular function. In particular examples, cardiac surgery requires the heart of the subject to be stopped, but this is not an absolute requirement of all forms of cardiac surgery. Particular examples of cardiac surgery include coronary artery bypass grafting surgery, aortic valve replacement or repair, mitral valve replacement or repair, tricuspid valve replacement or repair, ascending aorta replacement, heart transplantation, lung transplantation or any combination of the above.

Cardiopulmonary bypass (CPB): surgical technique for maintaining blood circulation and oxygenation when heart function is impaired or temporarily stopped. CPB is achieved through use of a pump. In particular examples, the pump is known as a "heart-lung machine," CPB pump, or CPB machine. In other examples, a type CPB is also known as "extracorporeal membrane perfusion."

Functional fragments and variants of a polypeptide: Included are those fragments and variants that maintain one or more functions of the parent polypeptide, such as a functional fragment or variant of AAT-1. It is recognized that the gene or cDNA encoding a polypeptide can be considerably mutated without materially altering one or more the polypeptide's functions. First, the genetic code is well-known to be degenerate, and thus different codons encode the same amino acids. Second, even where an amino acid substitution is introduced, the mutation can be conservative and have no material impact on the essential functions of a protein. Third, part of a polypeptide chain can be deleted without impairing or eliminating all of its functions. Fourth, insertions or additions can be made in the polypeptide chain for example, adding epitope tags, without impairing or eliminating its functions. Other modifications that can be made without materially impairing one or more functions of a polypeptide include, for example, in vivo or in vitro chemical and biochemical modifications or the incorporation of unusual amino acids. Such modifications include, for example, acetylation, carboxylation, phosphorylation, glycosylation, ubiquination, labeling, e.g., with radionucleides, and various enzymatic modifications.

Conservative amino acid substitution tables providing functionally similar amino acids are well known to one of ordinary skill in the art. The following six groups are examples of amino acids that are considered to be conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Variant amino acid sequences may, for example, be 80%, 85%, 90% or even 95% or 98% identical to the native AAT-1 amino acid sequence. Programs and algorithms for determining percentage identity can be found at the NCBI website.

Injectable composition: A pharmaceutically acceptable fluid composition comprising at least one active ingredient, for example, a protein, peptide, or antibody. The active ingredient is usually dissolved or suspended in a physiologically acceptable carrier, and the composition can additionally comprise minor amounts of one or more non-toxic auxiliary substances, such as emulsifying agents, preservatives, pH buffering agents and the like. Such injectable compositions that are useful for use with the compositions of this disclosure are conventional; appropriate formulations are well known in the art.

Organ injury: Impairment of normal organ function in a mammalian subject, including human and veterinary subjects. Organ injury as understood herein does not require complete loss of organ function. In particular examples, loss of specific organ function is diagnosed by detection of biological markers. For example, detection of liver enzymes is one indicator of liver injury.

Pharmaceutically acceptable carriers: The pharmaceutically acceptable carriers useful in this disclosure are conventional. *Remington's Pharmaceutical Sciences*, by E. W. Martin, Mack Publishing Co., Easton. Pa., 15th Edition (1975), describes compositions and formulations suitable for pharmaceutical delivery of the compounds herein disclosed. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pharmaceutical agent: A chemical compound or composition capable of inducing a desired therapeutic or prophylactic effect when properly administered to a subject.

Preventing or treating an injury: Preventing an injury refers to inhibiting the full development of an injury or pathological condition, for example inhibiting excessive post-operative bleeding or organ injury in a person who has or is undergoing cardiac surgery. Treatment refers to a therapeutic intervention that ameliorates a sign or symptom of the injury or pathological condition after it has begun to develop.

Resultant: An effect of a causative event is said to be "resultant" from that event. For example, in particular subjects, excessive bleeding is resultant from use of cardiopulmonary bypass in cardiac surgery. In particular examples, a resultant effect may immediately follow the causative event. In other examples, a resultant effect develops as a delayed response to the event. For example, certain organ damage may be resultant from use of cardiopulmonary bypass on a subject during cardiac surgery, but the extent of the damage may not be fully apparent for hours or even days after the surgery.

Subject: Living multi-cellular organisms, including vertebrate organisms, a category that includes both human and non-human mammals.

Therapeutically effective amount: A quantity of compound sufficient to achieve a desired effect in a subject being treated. An effective amount of a compound may be administered in a single dose, or in several doses, for example daily, during a course of treatment. However, the effective amount will be dependent on the compound applied, the subject being treated, the severity and type of the affliction, and the manner of administration of the compound.

III. Overview of Several Embodiments

Described herein are compositions including a therapeutically effective amount of alpha-1 antitrypsin (AAT-1), or a functional variant thereof, for use in preventing or treating injury to a subject during or resultant from cardiac surgery, and particularly from the use of cardiopulmonary bypass. In particular embodiments, the injury is excessive post-operative bleeding or organ injury.

In particular embodiments, the composition can be administered to the subject before the cardiac surgery, during the cardiac surgery, after the cardiac surgery or a combination thereof, in those embodiments wherein the composition is administered to the subject in multiple doses.

In some embodiments of the described composition, the concentration of AAT-1, or the functional variant thereof, is 1 gram in 50 cc sterile fluid in the form of a sterile or physiologically isotonic aqueous solution.

In some embodiments of the described composition, the AAT-1 is administered to the subject at a concentration of 30 to 300 mg per kg body weight per day. In other embodiments of the described composition, the AAT-1 is administered to the subject at a concentration of 60 to 100 mg per kg body weight per day.

In particular embodiments, the composition is administered as a single dose. In other embodiments, the composition is administered in multiple doses.

In some embodiments, the sole active ingredient of the composition is AAT-1. In other embodiments, the composition includes multiple active ingredients, and particularly at least one additional active ingredient for treatment of injury resultant from cardiac surgery. In still other embodiments, the additional one or more active ingredients is administered to the subject in an additional composition, which can be administered to the subject prior to, concurrent with, or after administration of the composition comprising AAT-1.

In particular embodiments the subject is human. In other embodiments, the subject is a veterinary subject.

Also described herein are methods for treating or preventing injury during or resultant from cardiac surgery in a human or veterinary subject, by administering to the subject a composition comprising a therapeutically effective amount AAT-1, or a functional variant thereof.

Particular embodiments of the described methods are directed to treatment or prevention of the injury resulting from use of cardiac bypass, including excessive post-operative bleeding or organ injury.

In particular embodiments, the composition is administered to the subject before the cardiac surgery, during the cardiac surgery, after the cardiac surgery or a combination thereof.

In some embodiments, the concentration of AAT-1, or functional variant thereof, in the composition is 1 gram in 50 cc sterile fluid in the form of a sterile or physiologically isotonic aqueous solution.

In particular embodiments, the AAT-1, or functional variant thereof, is administered to the subject at a concentration of 30 to 300 mg per kg body weight per day. In other embodiments, the AAT-1 is administered to the subject at a concentration of 60 to 100 mg per kg body weight per day.

In some embodiments, the AAT-1-containing composition is administered as a single dose. In other embodiments, the AAT-1-containing composition is administered in multiple doses.

In further embodiments, of the described methods, the composition comprises at least one additional composition for treatment of injury resultant from cardiac surgery. In other embodiments, the methods comprise administration of at least one additional composition which contain one or more active ingredients for treatment of injury resultant from cardiac surgery, which is administered to the subject prior to, concurrent with, or after administration of the composition comprising AAT-1.

IV. Cardiopulmonary Bypass

Cardiopulmonary bypass (CPB) during cardiac surgery elicits generalized non-specific systemic inflammatory response syndrome (SIRS), which initiates the activation of cytokine, complement, and coagulation-fibrinolytic cascades. In approximately 1% of all patients, depending on the number of organs involved, SIRS may result in severe multi-organ failure (MOF), having a mortality rate of 40-98%. Strategies used to attenuate the effects of SIRS focus on optimization of anaesthesiological, surgical, and CPB techniques.

During CPB, passage of blood through plastic tubing and through an oxygenator activates the clotting cascade, including activation of complement, cytokines, platelets, neutrophils, adhesion molecules, mast cells, and multiple inflammatory mediators. This can generate multi-organ system dysfunction that can manifest in a subject as post-operative respiratory failure, myocardial dysfunction, renal insufficiency, and neurocognitive defects.

The mechanism of damage to the lungs during cardiopulmonary bypass is unique. During CBP, blood flow through pulmonary circulation is minimal. This is followed by sequestration of neutrophils in the pulmonary capillary bed probably secondary to the lack of blood flow and the activation of pro inflammatory cytokines. The sequestered neutrophils, through the release of proteolytic enzymes, cause endothelial cell swelling, plasma and protein extravasation into the interstitial tissue, congestion of the alveoli with plasma, erythrocytes and inflammatory debris. Coagulation and inflammation are closely linked during cardiopulmonary bypass through networks of both humoral and cellular components including activation of proteases of the clotting and fibrinolytic cascades.

V. Methods for Inhibiting or Preventing Injury During or Resultant From Cardiac Surgery Described herein are methods of treating or preventing injury to a subject associated with cardiac surgery. The described methods involve administration of a composition comprising an effective amount of at least one dose of alpha 1 anti trypsin (AAT-1) prior to, concurrent with, or following cardiac surgery.

In particular embodiments the AAT-1-containing composition can be administered to the subject prior to the start of cardiac surgery such as 1, 2, 3, 4, 5 or more hours before surgery, including prior to administration of anesthesia or during pre-operative preparations. In other embodiments, the AAT-1-containing composition can be administered during cardiac surgery. In still other embodiments, the AAT-1 containing composition can be administered following the surgery, such as 1, 2, 3, 4, 5 or more hours after surgery, or 1, 2, 3, 4, 5 or more days following surgery In particular embodiments, the cardiac surgery involves use of cardiopulmonary bypass. In such embodiments, the at least one dose of AAT-1 is administered to the subject prior, current with, or after use of a cardiopulmonary bypass machine, but while the surgery is ongoing.

Cardiac surgery employing CPB can result in particular physiological pathologies in a subject, such as excessive post-operative bleeding and/or organ damage. The compositions and methods described herein can treat such pathologies, and therefore decrease the severity of the post-operative bleeding and/or organ damage. In particular examples, administration of an AAT-1 containing composition to a subject prior to, during, or following cardiac surgery employing CPB can prevent the injury. In such examples, post-operative bleeding is prevented from occurring as is organ damage. The development of post-operative bleeding and organ damage is determined by standard methods known to the art.

Alpha-1 Antitrypsin (AAT-1)

AAT-1 is a plasma-derived protein belonging to the family of serine proteinase inhibitors. AAT-1 is synthesized primarily in the liver, and to a lesser extent in other cells, including macrophages, intestinal epithelial cells and intestinal Paneth cells. In the liver, AAT-1 is initially synthesized as a 52 kD precursor protein that subsequently undergoes post translational glycosylation at three asparagine residues, as well as tyrosine sulfonation. The resulting mature protein is secreted as a 55 kD native single-chain glycoprotein. AAT-1, is also known as SERPINA-1. Nucleotide and amino acid sequences of human AAT-1 are available on-line at ncbi.nlm.nih.gov/nuccore/189163524 and ncbi.nlm.nih.gov/protein/NP_000286, respectively, and are included herein as SEQ ID NOs: 1 and 2.

AAT-1 is associated with control of tissue destruction by endogenous serine proteinases, and is the most prevalent serine proteinase inhibitor in blood plasma. AAT-1 inhibits, inter alia, trypsin, chymotrypsin, various types of elastases, skin collagenase, renin, urokinase and proteases of polymorphonuclear lymphocytes.

Patients with low circulating levels of AAT-1 are at increased risk for lung, liver, and pancreatic diseases, particularly emphysema. Accumulating data suggests that besides its ability to inhibit serine proteases, AAT-1 possesses independent anti-inflammatory and tissue-protective effects. AAT-1 modifies dendritic cell maturation and promotes regulatory T-cell differentiation, induces interleukin (IL)-1 receptor antagonist and IL-10 release, protects various cell types from cell death, inhibits caspases-1 and -3 activity and inhibits IL-1 production and activity.

Importantly, and contradictory to classic immune-suppressants. AAT-1 allows undeterred isolated T-lymphocyte responses. AAT-1 is currently used therapeutically for the treatment of pulmonary emphysema in AAT-1-deficient patients. AAT-1 deficiency is a genetic condition that increases the risk of developing a variety of diseases including pulmonary emphysema (Laurell and Eriksson Scand J Clin lab Inves 1963. 151132-140). AAT-1 deficiency is a result of mutations in the AAT-1-encoding gene (proteinase inhibitor (Pi) gene). Purified AAT-1 has been approved for replacement therapy (also known as "augmentation therapy") in such patients deficient in endogenous AAT-1.

AAT-1 is currently administered intravenously, and commercially-available AAT-1 preparations can be used in the methods and compositions described herein. For example, AAT-1 marketed under tradenames including Aralast® (Baxter Healthcare Corporation, Westlake Village, Calif.); Zemaira® (CSL Behring, King of Prussia, Pa.); Prolastin® (Grifols Therapeutics Inc., Clayton, N.C.); Trypsone® (Evaluate, Ltd); and Alfalastin®, and which are human AAT-1 formulations indicated for augmentation therapy in patients congenital deficiency of AAT-1 with clinically evident emphysema, can be used as described herein.

In addition to the commercially-available preparations, compositions comprising AAT-1 can be produced by standard protein expression and purification methodology known to the art and formulated for administration as described herein. It is also appreciated that functional variants of AAT-1 can be produced by standard methods of mutagenesis, which will maintain the activity of the wild type protein, and can be used in the compositions and methods described herein. Such functional variants can be identical in sequence to wild type AAT-1 by at least 98%, at least 95%, at least 90%, at least 85%, at least 80%, or even less than 80% identical.

Combination Therapies

In particular embodiments of the compositions and methods described herein. AAT-1 is combined with at least one additional active agent to treat or prevent injury resultant from excessive post-operative bleeding and/or organ damage. Non-limiting examples of active compounds for decreasing post-operative bleeding include fresh frozen plasma, platelets, cryoprecipitate, and alpha aminocaproic acid. Non-limiting examples of active compounds and procedures that can be used to decrease organ damage include steroids, and leucocyte depletion methods.

In some embodiments, the combination of AAT-1 and at least one additional active agent is administered to a subject in a single composition. In particular examples, the combination compositions are formulated so that the component active ingredients are simultaneously available in the subject in an active form. In other examples, the component active ingredients are formulated such that the components are sequentially available in an active form to the subject. For example, although administered simultaneously, the AAT-1 might produce the desired effect prior to the at least one additional compound.

In other embodiments, combinations of AAT-1 and at least one additional active agent can be administered to a subject in multiple compositions, one containing AAT-1 and at least one additional composition containing the at least one additional active agent. The timing and order of administration of such multiple compositions can vary, such as prior to, during, and after cardiac surgery, as described herein. In particular examples, the AAT-1-containing composition is administered prior to the additional composition. In other examples, the AAT-1-containing composition is administered simultaneously with the additional composition. In still other embodiments, the AAT-1-containing composition is administered after the additional composition. It is contemplated that when administered at separate times, significant time may elapse between administration of the at least two compositions, such as several hours, several days or even longer.

Pharmaceutical Compositions and Modes of Administration

The AAT-1 and other active agents for use in the described compositions and methods can be supplied in any pharmaceutically acceptable compositions. As described herein, AAT-1 is currently commercially available in several intravenous formulations.

Additionally, the pharmaceutical compositions specifically contemplated in the present disclosure can include pharmaceutically acceptable acid or base addition salts. The phrase "pharmaceutically acceptable acid or base addition salts" includes therapeutically active non-toxic acid and non-toxic base addition salt forms which at least some of the active agents described herein can form. Such compounds which have basic properties can be converted in their pharmaceutically acceptable acid addition salts by treating said base form with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

Those active agents which have acidic properties may be converted in their pharmaceutically acceptable base addition salts by treating said acid form with a suitable organic or inorganic base. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

Various delivery systems are known and can be used to administer peptide-based (such as AAT-1) and non-peptide active agents as therapeutics. Such systems include, for example, encapsulation in liposomes, microparticles, microcapsules, recombinant cells capable of expressing therapeutic molecule(s) (see, e.g., Wu et al., *J. Biol. Chem.* 262, 4429, 1987), construction of a therapeutic nucleic acid as part of a retroviral or other vector, and the like. Although current AAT-1 formulations are administered to subject intravenously, various alternative methods of administration of AAT-1 or additional active agents include, but are not limited to, intrathecal, intradermal, intramuscular, intraperitoneal (ip), intravenous (iv), subcutaneous, intranasal, epidural, and oral routes. The active agent therapeutics may be administered by any convenient route, including, for example, infusion or bolus injection, topical, absorption through epithelial or mucocutaneous linings (e.g., oral mucosa, rectal and intestinal mucosa, and the like) ophthalmic, nasal, and transdermal, and may be administered together with other biologically active agents. Pulmonary administration can also be employed (e.g., by an inhaler or nebulizer), for instance using a formulation containing an aerosolizing agent.

In a specific embodiment, it may be desirable to administer the described compositions by injection, catheter, suppository, or implant (e.g., implants formed from porous, non-porous, or gelatinous materials, including membranes, such as sialastic membranes or fibers), and the like. In another embodiment, therapeutic agents are delivered in a vesicle, in particular liposomes (see, e.g., Langer, *Science* 249, 1527, 1990; Treat et al., in *Liposomes in the Therapy of Infectious Disease and Cancer*, Lopez-Berestein and Fidler (eds.), Liss, N.Y., pp. 353-365, 1989).

In yet another embodiment, any one of the agents described herein can be delivered in a controlled release system. In one embodiment, a pump may be used (see, e.g., Langer *Science* 249, 1527, 1990; Sefton *Crit. Rev. Biomed. Eng.* 14, 201, 1987; Buchwald et al., *Surgery* 88, 507, 1980; Saudek et al., *N. Engl. J. Med.* 321, 574, 1989). In another embodiment, polymeric materials can be used (see, e.g., Ranger et al., *Macromol. Sci. Rev. Macromol. Chem.* 23, 61, 1983; Levy et al., *Science* 228, 190, 1985; During et al., *Ann. Neurol.* 25, 351, 1989; Howard et al., *J. Neurosurg.* 71, 105, 1989). Other controlled release systems, such as those discussed in the review by Langer (*Science* 249, 1527 1990), can also be used.

As described above, in particular examples wherein AAT-1 is administered with at least one additional active agent, the active agents are administered simultaneously, and by the same mode of administration. In other examples, the pharmaceutical compounds are administered at different times, and either by the same or different more of administration.

The vehicle in which the agent is delivered can include pharmaceutically acceptable compositions of the compounds, using methods well known to those with skill in the art. For instance, in some embodiments, described active agents typically are contained in a pharmaceutically acceptable carrier. The term "pharmaceutically acceptable" means approved by a regulatory agency of the federal or a state government or listed in the U.S. Pharmacopoeia or other generally recognized pharmacopoeia for use in animals, and, more particularly, in humans. The term "carrier" refers to a diluent, adjuvant, excipient, or vehicle with which the therapeutic is administered. Such pharmaceutical carriers can be sterile liquids, such as water and oils, including those of petroleum, animal, vegetable, or synthetic origin, such as peanut oil, soybean oil, mineral oil, sesame oil, and the like. Water is a preferred carrier when the pharmaceutical composition is administered intravenously. Saline solutions, blood plasma medium, aqueous dextrose, and glycerol solutions can also be employed as liquid carriers, particularly for injectable solutions. The medium may also contain conventional pharmaceutical adjunct materials such as, for example, pharmaceutically acceptable salts to adjust the osmotic pressure, lipid carriers such as cyclodextrins, proteins such as serum albumin, hydrophilic agents such as methyl cellulose, detergents, buffers, preservatives and the like.

Examples of pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The therapeutic, if desired, can also contain minor amounts of wetting or emulsifying agents, or pH buffering agents. The therapeutics can take the form of solutions, suspensions, emulsion, tablets, pills, capsules, powders, sustained-release formulations, and the like. The therapeutic can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, and the like. A more complete explanation of parenteral pharmaceutical carriers can be found in Remington: *The Science and Practice of Pharmacy* (19th Edition, 1995) in chapter 95.

Embodiments of other pharmaceutical compositions are prepared with conventional pharmaceutically acceptable counter-ions, as would be known to those of skill in the art.

Therapeutic preparations will contain a therapeutically effective amount of at least one active ingredient, preferably in purified form, together with a suitable amount of carrier so as to provide proper administration to the patient. The formulation should suit the mode of administration.

The compositions of this disclosure can be formulated in accordance with routine procedures as pharmaceutical compositions adapted for intravenous administration to human beings. Typically, compositions for intravenous administration are solutions in sterile isotonic aqueous buffer. Where necessary, the compositions may also include a solubilizing agent and a local anesthetic such as lidocaine to ease pain at the site of the injection.

The ingredients in various embodiments are supplied either separately or mixed together in unit dosage form, for example, in solid, semi-solid and liquid dosage forms such as tablets, pills, powders, liquid solutions, or suspensions, or as a dry lyophilized powder or water free concentrate in a hermetically sealed container such as an ampoule or sachette indicating the quantity of active agent. Where one or more of the indicated agents is to be administered by infusion, it can be dispensed with an infusion bottle containing sterile pharmaceutical grade water or saline. Where one or more of the indicated agents is to be administered by injection, an ampoule of sterile water or saline can be provided so that the ingredients may be mixed prior to administration.

Effective amounts can be determined by standard clinical techniques. The precise dose to be employed in the formulation will also depend on the route of administration, and should be decided according to the judgment of the health care practitioner and each patient's circumstances. Exemplary dosages of the individual compounds are described herein, but myriad other dosage regimens are encompassed by this disclosure. An example of an additional dosage range is 0.1 to 200 mg/kg body weight in single or divided doses. Another example of a dosage range is 1.0 to 100 mg/kg body weight in single or divided doses.

In particular embodiments. AAT-1 is provided in a composition at a concentration of 1 gram in 50 cc sterile fluid in the form of a sterile or physiologically isotonic aqueous solution. In particular embodiments a single dosage of AAT-1 administered to a subject at a dosage of 30 mg to 400 mg per kg body weight per day, such as 60 mg to 100 mg per kg body weight per day. In other embodiments, multiple comparable dosages of AAT-1 are administered to a subject in a combination of dosing periods prior to, during, or after cardiac surgery.

The specific dose level and frequency of dosage for any particular subject may be varied and will depend upon a variety of factors, including the activity of the specific compound, the metabolic stability and length of action of that compound, the age, body weight, general health, sex, diet, mode and time of administration, rate of excretion, drug combination, and severity of the condition of the host undergoing therapy.

In some embodiments, sustained localized release of the pharmaceutical preparation that comprises a therapeutically effective amount of a therapeutic compound or composition may be beneficial. Slow-release formulations are known to those of ordinary skill in the art. By way of example, polymers such as bis(p-carboxyphenoxy)propane-sebacic-acid or lecithin suspensions may be used to provide sustained localized release.

It is specifically contemplated in some embodiments that delivery is via an injected and/or implanted drug depot, for instance comprising multi-vesicular liposomes such as in DepoFoam (SkyePharma, Inc, San Diego, Calif.) (see, for instance, Chamberlain et al., *Arch. Neuro.* 50:261-264, 1993; Katri et al., *J. Pharm. Sci.* 87:1341-1346, 1998; Ye et al., *J. Control Release* 64:155-166, 2000; and Howell, *Cancer J.* 7:219-227, 2001).

The following examples are provided to illustrate certain particular features and/or embodiments. These examples should not be construed to limit the disclosure to the particular features or embodiments described.

EXAMPLES

Example 1: Single Dose Administration of Alpha-1 Anti-Trypsin for Treatment of Organ Injury and Postoperative Bleeding in Patients Undergoing Cardiac Surgery with Cardiopulmonary Bypass This example describes assay of AAT-1 as an effective inhibitor of injury to a subject undergoing cardiac surgery involving cardiopulmonary bypass. In particular, methods for determining the effect of AAT-1 on postoperative blood loss and organ-function assessment are described.
Methods
AAT-1 Dosage Previous studies and clinical practice indicated that the administration of multiple intravenous AAT-1 doses of 60 mg per kg body weight is safe (Wewers M D, et al., N Engl J Med., 316:1055-62, 1987). Such doing was found result in a low incidence of side-effects, with those reported being benign in nature. Based on pharmacokinetic studies, intraoperative administration of AAT-1 dosage (60 mg/Kg) results in AAT-1 plasma levels which resemble acute phase response; immediately following administration (Wewers M D, et al., N Engl J Med., 316:1055-62, 1987). A 30% reduction in plasma levels is anticipated after termination of CPB with gradual return to normal preoperative AAT-1 levels afterwards (Pickering N J et al., Am J Clin Pathol, 80:459-64, 1983).
Determination of Study Eligibility Patients eligible in a clinical study to assay use of AAT-1 are male or female, 40-70 years of age. Eligible patents are candidates for isolated coronary artery bypass grafting (CABG) employing cardiopulmonary bypass (CPB), have a calculated logistic Euroscore risk stratification of 5% or less, and will provide signed patient's written informed consent.

For the initial study, exclusion criteria will be based on presence of co-existing conditions including: coagulation abnormalities, severe pulmonary disease defined by blood oxygen saturation of 90% or less or FEV1 of less than 60% of predicted, renal dysfunction defined be serum creatinine levels higher or equal to 1.8 mg %, abnormal liver function tests, uncontrolled diabetes mellitus, severe peripheral vascular disease, a prior cerebrovascular neurological event, abnormal left or right ventricular function, and/or treatment with warfarin or thienopyridine class of anti-platelet agents.

The study participants are randomized to receive either single dose AAT-1 60 mg per kg or placebo.

Trial Medication Administration

Preparation and dosing of AAT-1 are performed by an unblinded pharmacist. The medication is diluted just prior to administration, and is selected from a commercially available AAT-1 preparation. The patients, research staff, laboratory personnel and data analysts remain blinded to the identity of the treatment from the time of randomization until database lock. Data unblinding is unnecessary. A randomization list is produced by the pharmacist, and was secured and confidential until time of unblinding.

The placebo solution comprises human albumin that resembles the color and consistency of the AAT-1 solution.

The medication is given 3-5 hours prior to surgery (skin incision). Administration rate of the drug does exceed 0.04 ml per kg per minute (for approximately 60-80 minutes). Vital signs including blood pressure, pulse rate and body temperature are correspondingly monitored.

Surgical Technique

Consistent with study center policy, fentanyl citrate (20-50 mcg/kg), midazolam (2-3 mg) and isoflurane (0.5-2%) are used for induction and maintenance of anesthesia.

Standard median sternotomy is performed followed by harvesting of bypass conduits, uni- or bilateral internal thoracic artery, radial artery or saphenous vein graft. Heparin loading dose is administered prior to initiation of cardiopulmonary bypass (CPB) to achieve kaolin activated coagulation time (ACT). Standard ascending aorta—right atrial cannulation is performed to institute CPB. CPB is initiated after verifying ACT level of 480 seconds or more and periodically monitored. Standard centrifugal pump and a membrane oxygenator are used for extracorporeal circulation (CPB). Consistent with standard technique, active systemic cooling is avoided and patients' core temperature ranges between 32 and 37° C. Distal anastomoses are performed during single aortic cross-clamp and blood cardioplegic arrest. Proximal anastomoses are performed during single aortic cross-clamp. Cold (10° C.) blood cardioplegic solution is delivered in a 4:1 ratio, in antegrade fashion via the aortic root with or without additional retrograde administration via the coronary sinus. After cardioplegic induction (10 ml/Kg) intermittent doses (300-500 ml) are administered; following completion of each distal anastomosis. Heparin is reversed using protamine sulphate in a ratio of 1:1 after weaning from CPB.

Data Collection

Preoperative data: Demographic, morphological and clinical descriptors including age, gender, body mass index (BMI), body surface area (BSA) co-morbidity, Euroscore risk-stratification, medication, etc. is recorded. Preoperative laboratory analysis includes complete blood count, coagulation profile, serum creatinine levels and creatinine clearance, liver function test and arterial blood gases test and serology for HIV, HCV, HBC. Compatible with our routine policy, all patients underwent preoperative echocardiography, coronary angiography, chest x-ray, lung function tests (spirometry) and carotid artery duplex study. Study participants are assigned to undergo preoperative brain MRI; and are subjected to the protocol described below.

Intraoperative: The type of surgery is categorized. The following data is recorded: heparin dose given prior to bypass initiation; activated clotting time (ACT) counts during the operation (prior, during and after CPB); operative time, cross-clamp time and CPB time; number of trials to wean from CPB, type of inotropes and dosage used during weaning from CPB; blood products utilization during surgery. Allergic reactions or adverse events observed by the surgeon or anesthesiologist are documented. The individual surgeon's impression regarding bleeding tendency is recorded.

Postoperative Organ Function and Blood Loss Evaluation

The occurrence and magnitude of systemic inflammatory response and organ dysfunction are recorded and quantified by laboratory markers. Related laboratory markers are monitored on a daily basis during the recovery period (in the intensive care unit and at the ward). The following organs and corresponding markers are monitored: Pulmonary function: Pulmonary function is evaluated by measured overall mechanical ventilation time, peak inspiratory pressures (PIP), plateau pressures, physiologic dead space and static and dynamic lung compliance. Bronchoalveolar lavage (BAL) is performed 3 hours after operation (while the patient is anesthesized and intubated) and extracted fluid is analyzed for inflammatory markers. A-a DO2 calculation $[AaDO_2=(713\times FiO_2)-(pCO_2/0.8)-(paO_2)]$ is measured daily. Complete pulmonary function test is performed before and 4 days after the operation. Chest radiographs are evaluated and quantified by an independent radiologist for the occurrence of atelectasis, pulmonary edema, or pleural changes.

Renal function: Renal function is evaluated by daily measurements of urine output, serum creatinine levels, creatinine clearance and urinary albumin levels. Acute kidney injury (AKI) markers are sampled in the ICU.

Brain injury assessment: The degree of insult to the brain is measured by plasma S-100 protein levels. Assessment of damage to the blood-brain barrier (BBB) is performed by magnetic resonance imaging (MRI) modality on post-operative days 1 and day 5. (see technique protocol below).

Hepatic function: Determined by daily measurements of serum hepatic enzymes levels.

Cardiac function: Cardiac function is monitored by assaying cardiac enzyme levels; need and magnitude of required inotrope treatment; occurrence of low cardiac output syndrome (defined as systolic blood pressure of 90 mmHg or less coupled with central venous pressure (CVP) of 15 mmHg or more), and incidence of cardiac arrhythmias. Transthoracic echocardiography examination is performed on postoperative day 5 and assessed by an independent cardiologist.

Blood loss: Operative and postoperative blood loss is monitored as well as daily hemoglobin levels. Daily platelet counts and thromboelastograms are performed. The distribution of blood products and total administered are recorded daily. Postoperative CRP levels are evaluated daily.

Blood sampling and laboratory analysis methods for cytokine levels: 10 mL whole blood venous EDTA samples are collected from radial artery catheter at five specified occasions: before induction of anaesthesia, 30 minutes after aortic cross-clamp positioning, and 3, 6, and 9 hours after aortic cross clamp positioning. The blood samples are subsequently centrifuged at 4° C. for 15 min and the serum stored at −70° C. Samples are analyzed for the following markers: Polymorphonuclear Neutrophil Elastase (PMNE), Interleukin-1α (IL-1α), Interleukin-1β (IL-1β), Interleukin-2 (IL-2), Interleukin-4 (IL-4), Interleukin-6 (IL-6), Interleukin-8 (IL-8), Interleukin-10 (IL-10), Interferon-γ (IFN-γ), Tumor Necrosis Factor-α (TNF-α), Vascular Endothelial Growth Factor (VEGF), Monocyte Chemoattractant Protein-1 (MCP-1), and Endothelial Growth Factor (EGF).

Daily blood samples are collected postoperatively for platelet count, renal function, liver function, CRP levels S-100 protein and troponin. Post-operative day 1 urine samples for acute kidney injury markers (N-GAL, KIM, Cistatin C) are collected.

Early post-operative adverse events are documented. These include 30-day mortality, new neurological events, myocardial infarction, renal dysfunction, need for re-exploration for bleeding and deep sternal wound infection.

Blood-Brain Barrier (BBB) assessment by MRI: The imaging modality used for BBB assessment is through use of a MRI scanner (Philips 3T or General Electric 1.5T). The examination format includes 24 cm FOV, 35 contiguous interleaved slices, 3.5-4 mm thick and co-localized across series. Trace-weighted DWI images are obtained at b=1000 from a 13-15 direction DTI sequence with an in-plane resolution of 2.5×2.5 mm and TR/TE=10 s/58 ms at 3T or TR/TE=10 s/72 ms at 1.5T. T2-FLAIR images are obtained with an in-plane resolution of 0.94×0.94 mm, TR/TE=9000/120 ms and TI=2600 ms at 3T or TR/TE=9000/140 ms and TI=2200 ms at 1.5T. (25).

Results 10 patients are recruited to the study. Five patients receive AAT-1 prior to surgery, and five patients receive placebo. Both groups are comparable with regard to preoperative and operative descriptors (parameters: age, sex, past medical history, left ventricular function, number of grafts performed during surgery and cardiopulmonary bypass time). There are no major operative events and postoperative complications are not observed in the cohort patients. Physical measurements described below are intended as approximations of expected results.

Inflammatory Parameters

Intra- and postoperative blood levels of IL-6, TNF-alpha, IL-1 beta, IL-8, MCP-1, LDH, and D dimmer increase in both groups. Elevation of these cytokines is significantly higher in the placebo group.

Nervous System

MRI at postoperative day (POD) 1 and POD 5 show significant BBB disruption (MR imaging-detected) in 60% of patients in the placebo compared to only 20% in the AAT-1 group. Acute major neurological deficit events are not detected in any patient.

S-100 protein on POD 1 increases by 3-fold in the placebo group compared to 1.5-fold in the AAT-1 group.

Respiratory System:

Postoperative BAL show significant increase in neutrophil elastase and TNF-alpha counts. Increase of these cytokines is twice more prominent in the placebo group.

Postoperative IL-8 levels decrease more in the placebo group. A-a DO2 decreases in all patients after surgery, more in the placebo group. The A-aDO2 returns to preoperative values on POD 3 in the AAT-1 group compared to POD 5 in the placebo group.

Lung function tests show substantial decrease in FEV-1 and TLC on POD 4 in the placebo group compared to almost no decrease in the AAT-1 group.

Postoperative chest x-rays show atelectasis in 3 of the 5 placebo group and non in the AAT-1 group.

Cardiovascular System

No signs of low cardiac output syndrome are recorded in any of the patients. Postoperative echocardiography show normal cardiac function in all patients.

Urinary System

Average preoperative creatinine is 1.0 mg/dL in both groups of patients. Postoperatively, the average creatinine rises to 1.3 mg/dL in the placebo group and remains 1 mg/dL in the AAT-1 group. Acute kidney injury markers, N-GAL KIM and Cystatin C, increase after surgery in all patients. The increase is substantially higher in the placebo group.

Fluid retention after operation as measured by daily body weight is more prominent in the placebo group (postoperative maximal increase in body weight was twice as much in the placebo group).

Liver Function

Blood liver enzymes levels increase postoperatively only in the placebo group

Post Operative Bleeding and Thrombocytes Function

Operative ACT levels are similar in both groups.

Post-operative bleeding is substantially lower in the AAT-1 group both 6 hours and 24 hours post operatively. Blood D dimmer levels as a marker of fibrinolysis increases more in the placebo group.

Postoperative thromboelastography shows signs of thrombocytes dysfunction in all patients (prolonged K and decreased MA); and more in the placebo group.

The AAT-1 group receives post-operatively about half the amount of blood products as compared to the placebo group.

Operative bleeding is also assessed by the individual surgeons' impression blinded to the medication and scaled from 1 to 10. The results show that patients in the AAT-1 group tended to bleed less.

Conclusion

The results of this randomized placebo controlled pilot study indicate that AAT-1 (administered and dosed as described) substantially attenuate CPB-inflicted organ injury. Post-operative bleeding and corresponding need for post-operative blood product administration are reduced. Administration of AAT-1 also appears to reduce post-CPB inflammation. Hospital length of stay is reduced reflecting improved overall patients' outcome.

Example 2: Multiple Dose Administration of Alpha-1 Anti-Trypsin (AAT-1) for Treatment of Organ Injury and Post-Operative Bleeding in Patients Undergoing Cardiac Surgery with Cardiopulmonary Bypass This example describes treatment of post-operative bleeding and organ damage resultant from cardiac surgery by administrations of multiple doses of AAT-1.

Except as specified herein, all methods are as described in Example 1.

As described above, AAT-1 is used to treat or prevent injury resultant from cardiac surgery with cardiopulmonary bypass. Example 1 describes such treatment with a single dose of a composition comprising AAT-1. In the current example, patients are administered two equivalent doses of AAT-1. As described in Example 1, the first dose is administered to the patient as part of the preoperative procedure. Following surgery, the subject is monitored for excessive bleeding and organ injury as described. At post-operative day 1-4, subjects presenting symptoms indicative of excessive bleeding and organ injury are administered a second dose of the composition comprising AAT-1.

Example 3: Combination Treatment of Organ Injury and Post-Operative Bleeding in Patients Undergoing Cardiac Surgery with Cardiopulmonary Bypass In this example, damage to a subject resultant from use of cardiopulmonary bypass in cardiac surgery is treated by administering to a subject a combination of AAT-1 and aminocaproic acid.

Methods are as described in the previous examples. In the current example, a subject undergoing cardiopulmonary bypass is administered a composition comprising AAT-1 as part of preoperative treatment. Following surgery, the subject is monitored as described for excessive bleeding and organ damage. A subject presenting symptoms of damage to the respiratory system, urinary system or nervous system is administered a second dose of AAT-1 at 60 mg per kg body weight in a composition containing an effective amount of aminocaproic acid for additional, complimentary treatment.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. I therefore claim as our invention all that comes within the scope and spirit of these claims.

I claim:

1. A method for preventing injury during or resulting from cardiac surgery in a subject, the method comprising administering to the subject 3 to 5 hours prior to start of a cardiac surgery a composition comprising a therapeutically effective amount of alpha-1 antitrypsin (AAT-1), thereby preventing injury during or resulting from cardiac surgery in a subject.

2. The method of claim 1, wherein the injury results from use of cardiac bypass.

3. The method of claim 1, wherein the injury comprises bleeding.

4. The method of claim 1, further comprising the step of administering the composition to the subject during the cardiac surgery, after the cardiac surgery or a combination thereof.

5. The method of claim 1, wherein the concentration of AAT-1 in the composition is 1 gram in 50 cc sterile fluid.

6. The method of claim 1, wherein the AAT-1 is administered to the subject at a dose of 30 to 300 mg per kg body weight per day.

7. The method of claim 1, wherein the AAT-1 is administered to the subject at a dose of 60 to 100 mg per kg body weight per day.

8. The method of claim 1, wherein the AAT-1 is administered in a single dose.

9. The method of claim 1, further comprising administering at least one additional active ingredient.

10. The method of claim 9, wherein the at least one additional active ingredient is administered to the subject prior to, concurrent with, or after administration of the composition comprising AAT-1.

11. The method of claim 1, wherein the subject is a human or a veterinary subject.

12. The method of claim 9, wherein the at least one additional active ingredient is for the prevention, treatment, or both of excessive post-operative bleeding and/or organ damage.

13. The method of claim 9, wherein the at least one additional active ingredient is: plasma, platelets, cryoprecipitant, alpha aminocaproic acid, or any combination thereof.

14. The method of claim 1, wherein the composition is an injectable composition.

15. The method of claim 1, wherein the cardiac surgery is selected from the group comprising: coronary artery bypass grafting surgery, aortic valve replacement or repair, mitral valve replacement or repair, tricuspid valve replacement or repair, ascending aorta replacement, heart transplantation, lung transplantation or any combination thereof.

* * * * *